United States Patent [19]

Yoshida et al.

[11] 4,061,780

[45] Dec. 6, 1977

[54] COSMETIC OIL CONTAINING ISOBUTYLENE

[75] Inventors: Moritoshi Yoshida, Chofu; Takashi Yamamoto, Yokohama; Sumito Nii, Fujisawa, all of Japan

[73] Assignee: Nichiyu Kagaku Co., Ltd., Tokyo, Japan

[21] Appl. No.: 632,578

[22] Filed: Nov. 17, 1975

Related U.S. Application Data

[63] Continuation of Ser. No. 425,617, Dec. 17, 1973, abandoned.

[30] Foreign Application Priority Data

Dec. 20, 1972  Japan .............................. 47-127823

[51] Int. Cl.$^2$ .................... A61K 47/00; A61K 7/025
[52] U.S. Cl. .................................... 424/358; 424/64; 424/83; 424/365
[58] Field of Search ................... 424/64, 83, 365, 358; 260/683.15

[56] References Cited

U.S. PATENT DOCUMENTS

| 2,628,187 | 2/1953 | Frohmader et al. | 424/83 |
| 3,211,619 | 10/1965 | Buchwalter et al. | 424/64 |

Primary Examiner—V. D. Turner
Attorney, Agent, or Firm—Blanchard, Flynn, Thiel, Boutell & Tanis

[57] ABSTRACT

Polymers of C4 olefins having a viscosity of 15 to 35 centistokes at 100° F show improved performance as cosmetic oils, in comparison with squalane. These polymers are prepared by polymerizing (a) isobutylene by itself, or (b) C4 hydrocarbon olefin containing a mixture of at least two of isobutylene, 1-butene, 2-butene and butadiene, using a catalyst; then removing high molecular weight and low molecular weight compounds by distillation; hydrogenating the remainder of the polymerization product; removing carbonyl compounds therefrom if necessary and further purifying the resultant polymer by steam distillation or treating same with activated carbon or solvent extraction, to deodorize same.

2 Claims, No Drawings

COSMETIC OIL CONTAINING ISOBUTYLENE

This is a continuation, of application Ser. No. 425,617, filed Dec. 17, 1973, now abandoned.

BACKGROUND OF THE INVENTION

1. Field of the Invention

This invention relates to cosmetic oils useful in cosmetic compositions.

2. Description of the Prior Art

It is known that squalane, which is obtained from purified shark oil, is useful as a base material for cosmetics. However, it is advantageous to use purified shark oil as a cosmetic oil because it is obtained from natural sources, the production thereof is low and the price thereof is high. Moreover, squalane is not uniform in quality. Therefore, it has been desired to prepare a synthetic oil having a performance in cosmetics superior to that of squalane.

SUMMARY OF THE INVENTION

A principal object of this invention is to provide a synthetic oil which is colorless and odorless, which has good stability, which permits good skin respiration and is non-irritating to human skin, which has good resistance to water and which is easily removable, the oil according to the invention being superior in these properties to squalane.

This invention provides a synthetic oil having a peroxide value, a bromine number, a carbonyl value and an acid value all of substantially zero. The viscosity of the synthetic oil is 15 to 35 centistokes (C.St.) at 100° F.

The synthetic oil according to the invention is prepared by polymerizing (a) isobutylene or (b) a mixture, such as a petroleum $C_4$ olefin fraction, consisting essentially of isobutylene and one or more of $C_4H_8$ and $C_4H_6$ mono- and di-olefin compounds including 1,2-butadiene, 1,3-butadiene, 1-butene and 2-butene, in the presence of a catalyst. From the polymerized reaction mixture there are removed, by distillation, (1) polymers having a molecular weight of less than about 250 as an initial fraction and (2) polymers having a molecular weight of more than about 600, as the still residue. There is obtained a polymer product having an average molecular weight in the range of about 250 to about 600 and essentially free of compounds having molecular weights of less than 250 and more than 600. This polymer product is purified and is hydrogenated. The thus-obtained product is colorless and odorless, it has good stability, it permits good skin respiration and, in general, possesses excellent characteristics as a cosmetic oil.

The liquid polymer of C4-olefins (hereinafter sometimes called "C4-polymer"), according to the invention, is a liquid polymer consisting essentially of polyisobutylene alone or polymer having various C4 olefin units including isobutylene in the molecular chain. The liquid polymer is obtained by polymerizing (1) isobutylene alone or (2) a mixture of isobutylene and one or more C4-olefins such as 1-butene, 2-butene and 1,2- and 1,3-butadiene. The polymerization is carried out at a temperature of from −30° to +60° C., using a Friedel-Craft's catalyst or Lewis acid such as $AlCl_3$, $FeCl_2$, $SnCl_4$, $BF_3$ and $ZnCl_2$.

It is preferred to employ a polymerization temperature of 20° to 50° C to obtain the desired C4-polymer having a viscosity of 15–35 centistokes at 100° F.

The liquid C4-polymer product is purified to obtain a purified product suitable for use as a cosmetic oil and having little or no impurities therein. The purification is carried out by the steps of: (1) removing unreacted gas, compounds having a molecular weight of less than about 250 and compounds having a molecular weight of more than about 600 by distilling the liquid C-4 polymer product under reduced pressure; (2) hydrogenating the product of step (1); (3) deodorizing and purifying the product of step (2) and (a) steam distillation under reduced pressure, or (b) treatment with activated carbon, or (c) solvent extraction, or combinations of steps (a), (b) and (c). Further, if carbonyl compounds are still present, they can be removed by treatment with activated clay, activated alumina, activated silica or molecular sieve, but this latter step is not usually required.

These purification steps shall be explained in further detail as follows:

1. Separation of unreacted gas, low and high molecular weight compounds;

Unreacted gas and compounds having molecular weights below about 250 are distilled off as an initial fraction. This initial fraction consists of compounds having boiling points of less than 120° C at 1–2 mmHg. The main fraction, i.e. the fraction having a boiling point range of 120° to 200° C at 1–2 mmHg and which contains the desired polymer is then distilled off, leaving compounds having boiling points of more than 200° C at 1–2 mmHg and having molecular weights above about 600 as the still residue. The main fraction is the crude material for obtaining the cosmetic oil of this invention.

The compounds contained in the initial fraction can easily oxidize to form odorous compounds such as aldehydes, ketones and the like, so that they must be substantially completely removed from the product of the polymerization step. The oxidation thereof in air is further accelerated in the presence of light, heat and water. Because these carbonyl compounds have strong odors and their presence in the cosmetic oil reduces the quality of the cosmetic oil of the invention, as much as possible of the light fraction should be removed by distillation. Such distillation is carried out until the initial fraction compounds cannot be detected by gas chromatography in the polymer product.

Compounds having molecular weights of more than 600 must also be removed because they detract from the ease of use and application of cosmetics containing the cosmetic oil according to the invention.

2. Hydrogenation

The polymer product obtained in step (1) is hydrogenated, using nickel or palladium as a catalyst, at 150° to 230° C, under a hydrogen pressure of 15 to 25 Kg/cm² to hydrogenate all of the double bonds thereof substantially.

3. Deodorization

The oily hydrogenated liquid C4 polymer obtained by step (2) is deodorized by (a) steam distillation under reduced pressure or (b) treatment with activated carbon or (c) solvent extraction, or combinations of steps (a), (b) and (c) to remove bad-smelling impurities. In the case of steam distillation, it is preferred to maintain the temperature of the polymer under 130° C in order to avoid deterioration of the polymer. Suitable solvents for removing impurities can be selected from among common organic solvents, including lower alkanols ($C_1$ to $C_3$), methylethylketone, acetone, etc. The solvent employed is not critical.

The final product, the cosmetic oil of this invention, is water white and odorless over a long period of time, it is non-irritating to human skin and it is pleasant to the touch. It can be spread on skin as easily as or more easily than squalane. This final product is a hydrogenated C-4 polymer oil having an average molecular weight in the range of 250 to 600. It is essentially free of compounds having molecular weights below 250 and above 600. It is also essentially free of carbonyl compounds and of impurities, particularly odor-causing substances.

It can be used in an amount of 3 to 50 wt. % as a base oil, in place of squalane, in conventional oil-based cosmetic compositions such as creams, lotions, lip sticks, hair oils, ointments, manicuring oils and the like. It will be understood that the present invention is not concerned with other ingredients of cosmetic compositions and they can be freely selected from ingredients suitable for cosmetic purposes, in accordance with conventional practice.

DESCRIPTION OF PREFERRED EMBODIMENTS OF THE INVENTION

The invention is further described by reference to the following illustrative Examples. It will be understood that the invention is not limited to the subject matter of the Examples. In the Examples all parts are by weight.

EXAMPLE 1

100 Parts of C4 olefins obtained by fractionation of petroleum and after removing most of the butadiene from the C4-cut, and 0.2 parts of aluminum chloride were heated at 30° C for 4 hours in a reactor.

The reaction product was distilled, the fraction having a boiling point of less than 120° C/1-2 mmHg was removed and the fraction having a boiling point of over 200° C/1-2 mmHg was separated as the still residue. 100 Parts of the remaining product from the distillation, i.e. the fraction having a boiling point range of 120° to 200° C at 1-2 mmHg, were hydrogenated for 6 hours at 160° C, and a hydrogen pressure of 17 Kg/cm² in an autoclave, using 5 parts of nickel on a silica support as catalyst. After completing the hydrogenation, the catalyst was removed by filtration.

The bromine number and the peroxide value of the hydrogenated product were zero and the chlorine content was 5 ppm. The product thus obtained was deodorized for 2 hours under a pressure of 2 mmHg and a temperature of 110° to 120° C by steam distillation.

The average molecular weight, viscosity, peroxide value, bromine number, carbonyl value and acid value of the final product are shown in Table 1.

EXAMPLE 2

Equal amounts of ethanol and the hydrogenated product obtained in Example 1 was refluxed for 1 hour. After separation of an ethanol layer, the remaining ethanol was removed by distillation, whereby the product was deodorized.

The average molecular weight, viscosity, peroxide value, bromine number, carbonyl value and acid value of the final product of Example 2 are shown in Table 1.

Further, the result of storage tests on the respective products is shown in Table 2. The storage tests were carried out by maintaining the respective products in a bath at 80° C. The peroxide value, carbonyl value, acid value and odor of the product were periodically checked during the storage.

Table 1

| Product No. | Average molecular weight | Viscosity at 100° F (centistokes) | Peroxide Value | Bromine no. | Carbonyl Value | Acid Value | Odor |
|---|---|---|---|---|---|---|---|
| Example 1 | 320 | 20 | 0 | 0 | 0 | 0 | none |
| Example 2 | 333 | 20.5 | 0 | 0 | 0 | 0 | none |
| Squalane | 392 | 18 | 0 | 0 | 0 | 0 | none |

Table 2
Storage test

| Property | Sample | 10 | 20 | 50 | 100 | 200 |
|---|---|---|---|---|---|---|
| Peroxide Value | A | 0.0 | 0.0 | 0.0 | 0.0 | 0.2 |
| | B | 0.0 | 0.0 | 0.0 | 0.01 | 0.2 |
| | C | 0.0 | 0.0 | 0.0 | 0.05 | 0.3 |
| Carbonyl Value | A | 0.0 | 0.0 | 0.1 | 0.1 | 0.1 |
| | B | 0.0 | 0.0 | 0.1 | 0.1 | 0.1 |
| | C | 0.0 | 0.0 | 0.1 | 0.1 | 0.1 |
| Acid Value | A | 0.0 | 0.0 | 0.0 | 0.0 | 0.1 |
| | B | 0.0 | 0.0 | 0.0 | 0.0 | 0.1 |
| | C | 0.0 | 0.0 | 0.0 | 0.0 | 0.1 |
| Odor | A | none | none | none | none | none |
| | B | none | none | none | none | none |
| | C | none | none | none | none | very slight |

A : Sample of Example 1
B : Sample of Example 2
C : Squalane

Subsequently, animal and human body tests with the product obtained in Example 1 were carried out as follows.

a. Primary Skin Irritation Test (Animal Test)

The influence on animal skin was observed at 24 hours and 48 hours after applying this product to six rabbits of 2-3 Kg weight. No irritation of the erythema, eschar and edema was found on intact or abraded rabbit skins.

b. Primary Skin Irritation Test (Human Body Test)

The results of patch tests carried out by direct application of various test materials to the skins of 50 adult men and women show that the skin irritation effect of the product of the invention on human skins was nil, as shown in Table 3. The test results were judged with the naked eye.

Table 3

| | Primary Skin Irritation Test | |
|---|---|---|
| Sample | Animal Test | Human Body Test |
| 1. This invention (Example 1) | 0.00 | 0/50 |
| 2. Squalane | 0.00 | 0/50 |
| 3. Unpurified polymer | 0.62 | 1/50 |

Further, the test result of the acute oral toxicity of the product of Example 1 on mice was as follows:

Acute Oral Toxicity—($LD_{50}$) to 69.9 g/Kg

The result of eye irritation on rabbits was negative.

As mentioned above, the purified polymer of C4 olefin according to this invention is extremely superior to the unpurified polymer in respect of primary skin irritation, eye irritation, and acute oral toxicity properties.

The storage tests of Table 2 and the results shown in Tables 1 and 3 show that the C4 polymer according to this invention is equal to or superior to squalane for use as a cosmetic oil.

The following recipes illustrate the use of the C4 polymers of this invention in the preparation of representative, illustrative cosmetic compositions.

EXAMPLE 3 Cold Cream composition

The C4 polymers obtained according to Example 1 and the other ingredients described below were mixed to prepare a cold cream.

| Component | wt.% |
|---|---|
| C4 polymer of this invention (Example 1) | 12.0 |
| liquid paraffin 70 | 20.0 |
| beeswax | 12.0 |
| cetyl alcohol | 6.0 |
| isopropyl myristate | 5.0 |
| glyceryl monostearate | 3.0 |
| polyoxyethylene sorbitanmonooleate | 3.0 |
| propylene glycol | 3.9 |
| potassium hydroxide | 0.1 |
| water | 30.0 |
| perfume & methyl paraben | 0.5 |

The thus-obtained cold cream is superior to a cold cream obtained by mixing the same chemicals as used in Example 3, but employing the same amount of squalane in place of the C4 polymer, in the properties of freedom from color and odor, stability, skin respiration, pleasant touch and ease of application.

EXAMPLE 4 Hygienic Cream composition

The liquid C4 polymer of Example 1 and the other ingredients listed below were mixed to prepare a hygienic skin cream.

| Component | wt. % |
|---|---|
| C4 polymer of this invention (Example 1) | 10.0 |
| stearic acid | 10.0 |
| isostearic acid | 5.0 |
| lanolin | 2.5 |
| steary alcohol | 5.0 |
| glyceryl monostearate | 3.0 |
| polyoxyethylene sorbitanmonopalmitate | 3.0 |
| glycerine | 2.0 |
| triethanolamine | 1.0 |
| water | 58.0 |
| perfume & preservative | 0.5 |

The thus-obtained hygienic cream is superior to the comparison one prepared by mixing the same chemicals as used in Example 4, but using squalane in place of the C4 polymer, in the same characteristics as described in Example 3.

EXAMPLE 5 Body Lotion composition

The liquid C4 polymer of Example 1 was mixed with the following ingredients to prepare a body lotion composition.

| Component | wt. % |
|---|---|
| C4 polymer of this invention (Example 1) | 14.0 |
| lanolinic acid | 2.0 |
| polyethylene oleic ether | 3.0 |
| glyceryl monostearate | 1.0 |
| glycerine | 4.0 |
| water | 76.0 |

The thus-obtained body lotion composition is superior to the comparison one prepared by mixing the same chemicals as used in Example 5, but using squalane in place of the C4 polymer, in the same charateristics as described in Example 3.

EXAMPLE 6 Lip Stick composition

The liquid C4 polymer of Example 1 was mixed with the following chemicals to prepare a lip stick composition.

| Component | wt. % |
|---|---|
| C4 polymer of this invention (Example 1) | 5.0 |
| beeswax | 13.0 |
| microwax | 3.0 |
| gswax | 2.0 |
| carnauba wax | 2.0 |
| lanolin | 5.0 |
| hydrogenated cottonseed oil | 5.0 |
| castor oil | 40.0 |
| isostearyl alcohol | 12.0 |
| propylene glycol monoricinoleate | 6.0 |
| pigment & perfume | 7.0 |

The thus-obtained lip stick composition is superior to the one prepared by mixing the same chemicals as used in Example 6, but using squalane in place of C4 polymer, in the same characteristics as described in Example 3.

The embodiments of the invention in which an exclusive property or privilege is claimed are defined as follows:

1. An oil-based cosmetic composition containing from 3 to 50 percent by weight of a cosmetic oil and the balance is conventional cosmetic ingredients for oil-based cosmetic compositions, said cosmetic oil having been prepared by polymerizing a substance consisting essentially of isobutylene or a mixture of isobutylene and one or more olefins selected from the group consisting of 1-butene, 2-butene, 1,2-butadiene and 1,3-butadiene, at a temperature of from $-30°$ to $+60°$ C, in the presence of a Friedel-Craft's catalyst or Lewis acid, to obtain a crude liquid polymer product; distilling said crude liquid polymer product under reduced pressure to separate materials having boiling points of less than 120° C at 1 to 2 mmHg and materials having boiling points of more than 200° C at 1 to 2 mmHg, and recovering a purified polymer product having a boiling point range of from 120° to 200° C at 1 to 2 mmHg and having an average molecular weight in the range of from about 250 to about 600; hydrogenating said purified polymer product to hydrogenate substantially all the double bonds in said purified polymer product; and deodorizing said hydrogenated purified polymer product to obtain said cosmetic oil by one of the steps of (1) steam distilling the hydrogenated purified polymer product under reduced pressure at a temperature below 130° C, or (2) treating the hydrogenated purified polymer product with activated carbon, or (3) effecting solvent extraction of the hydrogenated purified polymer product, or combinations of steps (1), (2) and (3), to remove impurities from the hydrogenated purified polymer product, said cosmetic oil having an average molecular weight in the range of from 250 to 600 and being substantially free of materials having molecular weights below 250 and above 600, said cosmetic oil being colorless and odorless, having a peroxide value, a bromine number, a carbonyl value and an acid value all of substantially zero, and having a viscosity of from 15 to 35 centistokes at 100° F.

2. An oil-based cosmetic composition according to claim 1 in which said substance consists essentially of isobutylene.

* * * * *